United States Patent [19]
Luongo et al.

[11] 3,935,730
[45] Feb. 3, 1976

[54] METHOD AND GAUGE FOR NONDESTRUCTIVELY TESTING AND CERTIFYING THE WORKABLE QUALITIES OF A CASTING

[75] Inventors: Albert Michael Luongo, Edison; Frank J. Reynolds, North Brunswick; Rudolph R. Ruetsch, Union, all of N.J.

[73] Assignee: Thomas & Betts Corporation, Elizabeth, N.J.

[22] Filed: Oct. 2, 1974

[21] Appl. No.: 511,170

[52] U.S. Cl. .................. 73/100; 73/87; 174/71 R; 174/94 R
[51] Int. Cl.² ................................................ G01N 3/20
[58] Field of Search ................ 73/87, 100, 88 R; 174/71 R, 94 R

[56] References Cited
UNITED STATES PATENTS

| | | | |
|---|---|---|---|
| 2,707,775 | 5/1955 | Hoffman et al. | 174/94 R |
| 3,322,888 | 5/1967 | Zemels | 174/94 R |

*Primary Examiner*—James J. Gill
*Assistant Examiner*—Anthony V. Ciarlante
*Attorney, Agent, or Firm*—David Teschner; Jesse Woldman

[57] ABSTRACT

The invention is directed to a method and gauge for nondestructively testing and certifying the workable qualities of a casting. The guage comprises a tab cast at the same time as the remaining portion of the casting located in a nonfunctional location, when considered in the light of the later use to be made of the casting, and also in such a position that it can be bent as by striking with a percussive instrument or by the application of a continuous bending force without damage to the remaining portion of the casting. The tab or guage will be subjected to a strain greater than the maximum strain to which the remaining portion of the casting will be subjected, during its installation or use, and determining by visual inspection whether or not the tab, at its bend has cracked, the overall ductility of the casting can be judged and it can be projected, that the casting will be able to withstand the forces to which it will be subjected when employed in a desired manner. The tab will take on a generally rectangular configuration of prescribed minimum height, width, and thickness, such that it may be correctly subjected to strain forces in excess of the strain forces to be applied to the casting during its normal use or installation.

7 Claims, 6 Drawing Figures

METHOD AND GAUGE FOR NONDESTRUCTIVELY TESTING AND CERTIFYING THE WORKABLE QUALITIES OF A CASTING

BACKGROUND OF THE INVENTION:

1. Field of the Invention:

The invention finds utility in the testing and certification of castings to determine in a nondestructive manner the workable qualities thereof.

2. Description of the Prior Art:

According to prior art techniques, castings were visually inspected once they had been taken out of the mold to determine the presence of cracks, inclusions, voids, and the like. A further test for voids was the grinding of the ingate, that part of the casting where the molten metal is poured into the mold, inspecting the same for pock marks which is indicative of the presence of voids and would tend to indicate their presence in the remaining portion of the casting. Certain sophisticated X-ray techniques can be employed to discover defects in the structure of the casting which includes foreign material, the present of large voids inside of the casting or unusual shapes or structure within the casting itself. However, with such techniques it is generally not possible to determine hydrogen embittlement or other undesirable characteristics that decrease the amount of plastic flow within the casting. The amount of plastic flow or ductility of the casting is important to the overall performance of the casting, if the casting is to be used in the electrical industry, where low electrical resistance at the wire terminal interface depends on the degree mechanical bond between the conductor and the terminal itself. Further, the presence of defects in the casting, such as cracks, become important when the casting is exposed to the environment, as by being left in the air in a overground installation or being buried underground within the soil itself. The presence of moisture, acids and other material, present in both the air and the ground, are able to penetrate the junction through these cracks and attack connector and the conductor itself and thus lead to the destruction of the joint. However, long prior to the actual destruction or the mechanical breaking of the joint, the electrical conductivity of the joint will be effected and the joint will become what is known as a hot contact or high resistance contact detrimental to the electrical system of which it is a part. Sampling techniques are not generally applicable to batch testing of castings, in that each casting is separate and discrete having been subjected to possibly different temperatures and pressures as the material is heated, poured, and the casting is allowed to cool.

SUMMARY OF THE INVENTION:

The present invention makes possible the testing of each and every casting in a nondestructive manner to certify its workable qualities, when later installed. A guage is provided upon each casting and the guage is located in such a manner so as not to be part of the functional characterists of the casting, when it is later employed and also in such a location as to be easily struck with a percussive instrument. The guage or tab is constructed in a generally rectangular configuration having prescribed ranges of width, thickness, and height. The most effective guage or tab has thickness and width minimums and shows a height to thickness ratio equal to approximately three. A properly configured guage or tab when struck with a percussive instrument, will bend from its position normal to a surface of the casting to a new position at approximately 90° from its original position or parallel with the casting surface. The strain to which such guage or tab is subjected as a result must be higher than the strain present in any part of the casting when the casting is put into use. The bend of the guage or tab is then inspected for signs of cracking although some slight crazing is acceptable. Should no cracking occur at the guage or tab bend, the casting as a whole, will have sufficient ductility and will be of such workable quality that it will not crack when it is crimped to or compressed around an electrical conductor. Any casting whose guage or tab shows cracking can then be disposed of before use. If the testing is done before any expensive machining of the casting is done, much time and expense can be avoided. If the test is done prior to use, the effort and time required to remove a cracked installed connector is saved. The guage or tab may be left in place after bent for certification purposes to all who later see the casting or removed as is desired. It is therefore an object of this invention to provide a guage or tab for the nondestructive testing and certifying of the workable qualities of a casting.

It is another object of this invention to teach a method by which a casting may be nondestrictively tested and certified for its workable qualities.

It is yet another object of this invention to provide a method and guage or tab for the nondestructive testing and certifying of the workable qualities of a casting which guage or tab is located upon the casting and formed at the same time as the casting, and which guage or tab is located in a position which will not interfere with the later functioning of the casting, and which can be subjected to a strain greater than the overall casting when employed.

Another object of the invention is to provide a method and guage for the determination of the ductility of a casting.

Other objects and features of the invention will be pointed out in the following description and claims and illustrated in the accompaning drawings, which disclose, by way of example, the principles of the invention and the best mode, which has been contemplated for carrying it out.

BRIEF DESCRIPTION OF THE DRAWINGS:

In the drawings in which similar elements are given similar reference characters.

Figure 1:
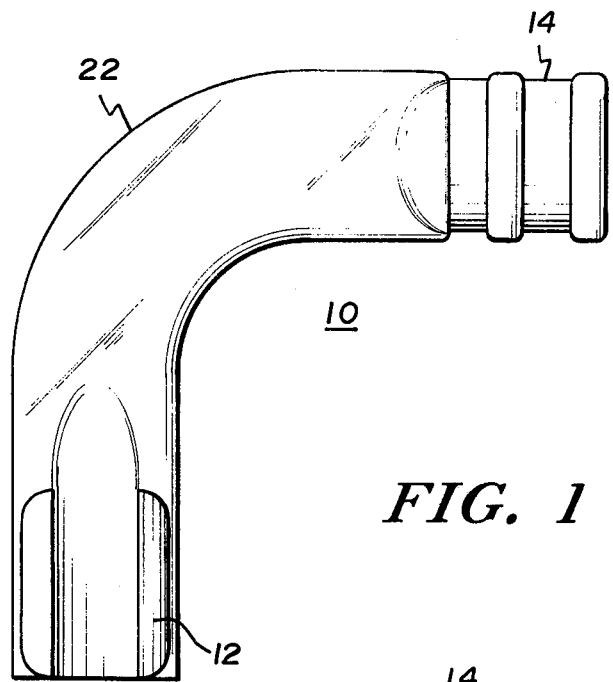
FIG. 1 is a top plan view of a connector formed by machining a casting, which includes a guage or tab constructed in accordance with the concepts of the invention.
Figure 2:
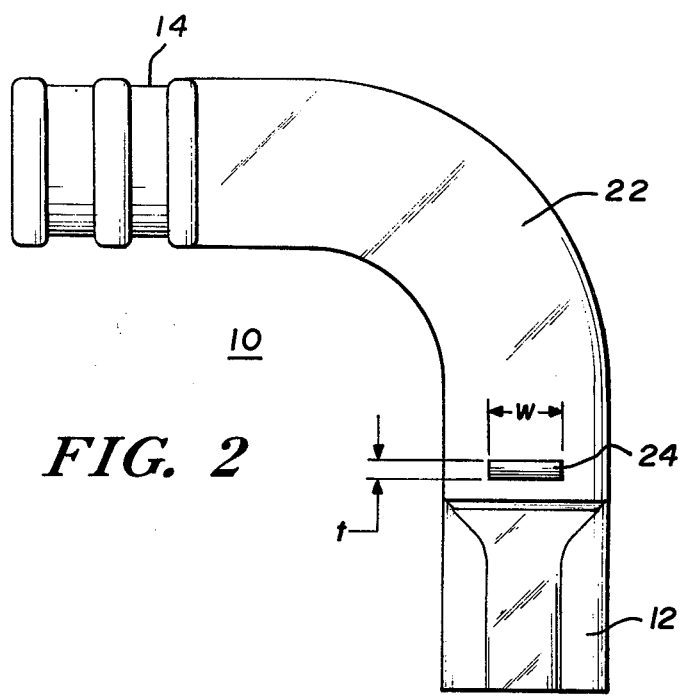
FIG. 2 is a bottom plan view of the connector of FIG. 1.
Figure 3:
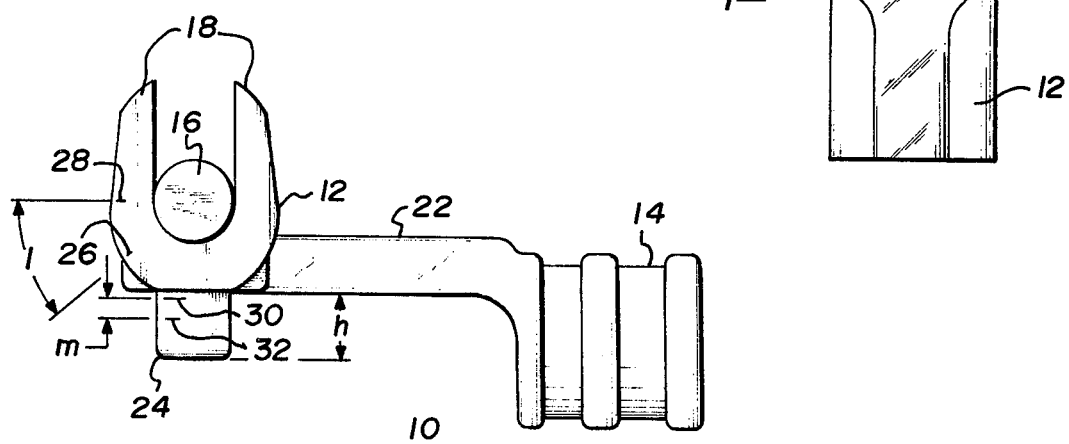
FIG. 3 is a front elevational view of the connector of FIG. 1, showing a conductor placed in its open seamed nest.
Figure 4:
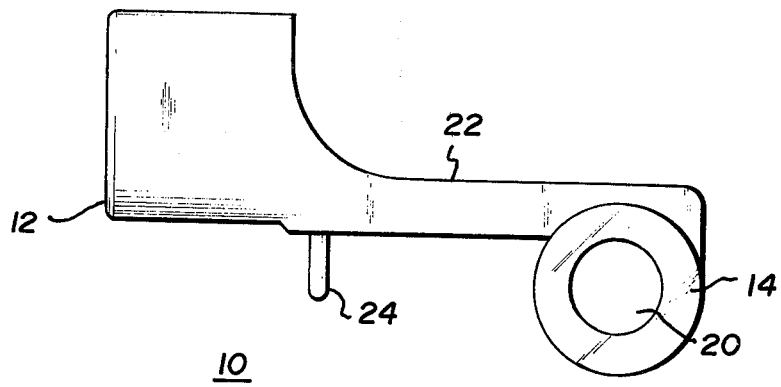
FIG. 4 is a side elevational view of the connector of FIG. 1.

DESCRIPTION OF THE PREFERRED EMBODIMENTS:

Turning now to FIGS. 1, 2, 3, and 4, there is shown a connector 10 constructed from a casting and displaying a guage or tab constructed in accordance with the concepts of the invention. Connector 10 has a U-shaped open conductor receiving portion 12 at a first end with a fully enclosed circular conductor receiving portion 14 at its opposite end, as is best seen in FIG. 3. A conductor such as the conductor 16 is inserted into the U-shaped open conductor receiving portion 12 between the upstanding arms 18. The arms 18 will then be crimped about the conductor 16 so as to provide an intimate contact between the conductor 16 and the connector 10. Further, a conductor (not shown) is inserted within the bore 20, of the circular conductor receiving portion 14, and the conductor receiving portion 14, then crimped to join the connector 10 to this conductor. A web portion 22 connects the U-shaped open conductor portion 12 and the circular closed conductor receiving portion 14. The web portion 22 serves no other purpose but to electrically connect the U-shaped open conductor receiving portion 12 and the circular closed conductor receiving portion 14 and to position these two sections with respect to one another and with respect to the conductors to which they are to be joined.

It is within the area of the web portion 22 that the tab 24 used as the basis for determining constructively the workable qualities of the casting is located. Should the tab 24 be located below the U-shaped open conductor receiving portion 12, or within or outside of the circular closed conductor receiving portion 14, the presence of the guage or tab would have an effect upon the crimping forces to be employed in these regions and may prevent the portions from properly seating themselves within a die used to crimp the connectors to a conductor placed therein. However, there is is no requirement for working any portion of the web portion 22, and thus, the location of the guage or tab 24, within the web portion 22, is non-functional with respect to the use to which the connector 10, is to be placed later. Guage or tab 24 will have certain physical dimensions, such that the proper relationship between the strain which the tab 24 is subjected is higher than the strain to which any part of the connector 10 is subjected. As shown in FIG. 2, the tab 24 will have a width indicated by the letter $w$ and a thickness indicated by the letter $t$ and also as is shown in FIG. 3, the tab 24 will have a height indicated by the letter $h$.

Figure 5:
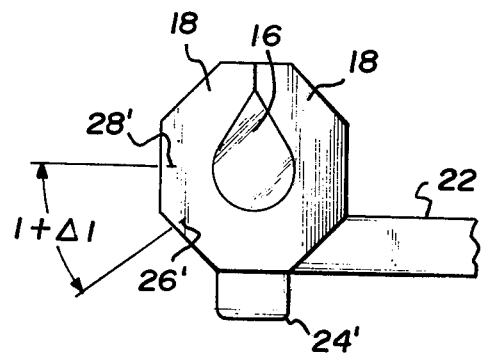
FIG. 5 is a fragmentary front elevational view of the connector of FIG. 1 with a portion of the connector crimped about a conductor.
Figure 6:
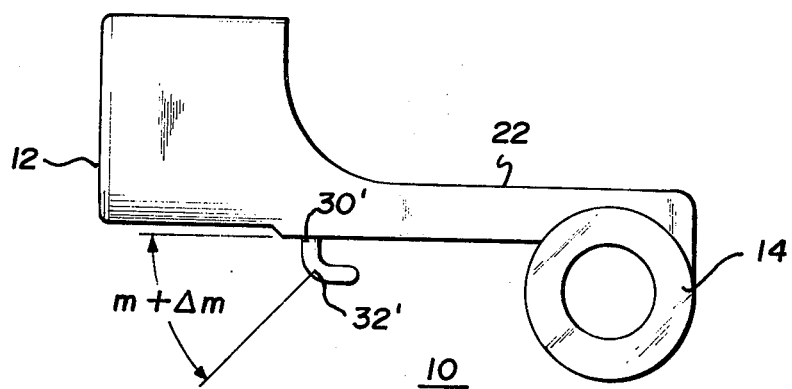
FIG. 6 is a side elevational view of the connector of FIG. 4 with the guage or tab in its final position after being struck by a percussive instrument.

To measure the strain, the U-shaped open connector portion 12 will be subjected to marks 26 and 28, are scribed upon the upstanding arm 18. The distance between the marks 26 and 28 is then measured prior to the time that the U-shaped open connector portion 12 is crimped to the conductor 16 placed therein and recorded as the letter l as indicated by the letter l in FIG. 3. When the U-shaped open conductor receiving portion 12 has been compressed or crimped about the conductor 16, as seen in FIG. 5, the positions of the scribed marks 26 and 28 have been shifted to the new positions 26' and 28', as shown in FIG. 5. A certain degree of stretching will take place within the sidewalls 18, as they are compressed about conductor 16, resulting in a new length "l + 1", as shown in FIG. 5. The strain to which the U-shaped open conductor receiving cavity 12 is thus subjected can be determined by dividing the resulting increase in length "$\Delta l$" by the original length l. The strain to which the guage or tab 24 will be subjected will similarly be determined by the use of scribe marks 30 and 32 as shown in FIG. 3. Scribe mark 30 is very close to the junction between the guage or tab 24 and the main body of the U-shaped open conductor receiving portion 12 and the scribe mark 32 will be somewhere beyond the expected bend of the guage or tab 24 and the distance therebetween is indicated by the letter $m$ in FIG. 3. When the guage or tab 24 has been subjected to bending forces, it will bend to the position as shown in FIG. 6 as 24'. As a result of the bending, the guage or tab 24 will tend to stretch and a new distance between the marks 30' and 32' will measure as $m + \Delta m$. The strain applied to the guage or tab 24, will be determined as above by dividing $\Delta m$ by $m$.

The dimensions of the guage or tab 24 is so selected that the strain applied to the tab 24, will be greater than the strain applied to either the U-shaped open conductor receiving portion 12 or the closed circular conductor receiving portion 14. Thus, if the guage or tab 24 does not show cracking when subjected to a higher strain than the remaining portion of the casting, it can reasonably be assumed that the casting will resist cracking during its installation to the conductors. In order that the proper strain relationship be established between the guage or tab 24 and the remaining portion of the connector 10, it has been found the guage or tab 24 should have a thickness at least equal to 0.05 inch as molten metal during the casting operation may not flow to properly fill the entire void of such a mold, if the dimension is smaller. Failure to fill this portion of the mold could result in a guage or tab 24 which could easily be broken from the casting without giving proper indication of the workable qualities of the remaining portion of the casting. Also, the width of the guage or tab 24 must be at least 0.10 inch, and can extend to the entire width of the casting, if so desired. Finally, the relationship between the height and thickness of the guage or tab 24, have been established to be approximately equal to 3. Should the height of the guage or tab 24 be less than this, the strain applied to the guage or tab 24 during testing, would be so high as to insure that it would break at all times and fail to give a proper indication of the quality of the casting. Also, a guage or tab 24 of too great height H would produce to lower strain that would result in a long gentle bend which would never crack and thus would also fail to give a proper indication of the quality of the casting. It is possible for particular operations to bend the guage or tab 24 less than a full 90°, as shown in FIG. 6, when a lower ductility of the finished casting is permissible, or installation forces to be applied to the casting are below those normally required with its own design characteristics. A suitable test will then be possible with only a partial bending of the guage or tab 24. Also, by measuring the degree of bending of the tab 24 before cracking has taken place, it is possible to get an index of the relative ductility of the casting as well.

While there have been shown, described and pointed out the fundamental novel features of the invention, as applied to the preferred embodiments, it will be understood that various ommissions and substitutions and changes in form and details of the device illustrated and its operation may be made by those skilled in the art, without departing from the spirit of the invention.

The embodiments of the invention in which an exclusive property or privilege is claimed are defined as follows:

1. The method of nondestructive testing and certifying the workable qualities of a cast metallic part comprising: the steps of forming a tab on said cast metallic part in a nonfunctional location, when considered in light of the intended use of said cast metallic part subjecting said tab to a strain greater than the strain to which the cast metallic part will be subjected to when employed; inspecting said tab after said tab has been subjected to said strain, and discarding any cast metallic part whose strained tab shows signs of cracking.

2. The method of claim 1 wherein said tab is formed in a generally rectangular configuration having a height to thickness ratio of approximately 3.

3. The method of claim 1, wherein said tab has a minimum thickness of 0.05 inches.

4. The method of claim 1, wherein said tab is formed in a generally rectangular configuration having a height to thickness ratio of approximately 3 and the minimum thickness of said tab in 0.05 inches.

5. The method of claim 1, wherein said tab has a minimum width of about 0.1 inches.

6. The method of claim 1, wherein said tab is formed in a generally rectangular configuration having a height to thickness ratio of approximately 3 and the minimum width of said tab is about 0.1 inches.

7. The method of claim 1, wherein said tab is formed in a generally rectangular configuration having a height to thickness ratio of approximately 3; said tab having a minimum thickness of 0.05 inches and a minimum width of about 0.1 inches.

* * * * *